United States Patent
Baltimore et al.

(10) Patent No.: US 6,994,967 B1
(45) Date of Patent: Feb. 7, 2006

(54) TRANSCRIPTION FACTOR REGULATORS AND METHODS FOR SCREENING FOR SAME

(75) Inventors: David Baltimore, Pasadena, CA (US); Joel L. Pomerantz, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 284 days.

(21) Appl. No.: 09/900,509

(22) Filed: Jul. 5, 2001

Related U.S. Application Data

(60) Provisional application No. 60/238,479, filed on Oct. 6, 2000, provisional application No. 60/215,779, filed on Jul. 5, 2000.

(51) Int. Cl.
*C12Q 1/68* (2006.01)
(52) U.S. Cl. .......................................... 435/6; 435/69.1
(58) Field of Classification Search .................... 435/4, 435/6, 69.1, 320.1, 325; 536/23.1, 23.5; 530/300, 350
See application file for complete search history.

(56) References Cited

U.S. PATENT DOCUMENTS

| 5,958,671 A | * | 9/1999 | Glimcher et al. | ............... 435/4 |
| 2002/0098477 A1 | * | 7/2002 | Kushner et al. | ............... 435/6 |

FOREIGN PATENT DOCUMENTS

WO WO 99/11760 * 3/1999

* cited by examiner

*Primary Examiner*—Kenneth R. Horlick

(74) *Attorney, Agent, or Firm*—Richard F. Trecartin

(57) ABSTRACT

Described herein are methods of expression cloning of components of signaling pathways that activate a transcription factor of interest. The methods are efficient for identifying modulators of transcription factors. The modulators can then be screened further or used directly to develop therapeutics.

12 Claims, 3 Drawing Sheets

SEQUENCE LISTING

<160> NUMBER OF SEQ ID NOS: 3

<210> SEQ ID NO 1
<211> LENGTH: 10
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: "n" at position 5 can be any base.

<400> SEQUENCE: 1 gggrnyyycc                                                          10

<210> SEQ ID NO 2
<211> LENGTH: 11
<212> TYPE: DNA
<213> ORGANISM: Artificial sequence
<220> FEATURE:
<223> OTHER INFORMATION: synthetic

<400> SEQUENCE: 2
ggggactttc c                                                        11

<210> SEQ ID NO 3
<211> LENGTH: 11
<212> TYPE: DNA
<213> ORGANISM: Artificial sequence
<220> FEATURE:

-continued

```
<223> OTHER INFORMATION: synthetic

<400> SEQUENCE: 3
atccactttc c                                                          11
```

US 6,994,967 B1

TRANSCRIPTION FACTOR REGULATORS AND METHODS FOR SCREENING FOR SAME

This application claims the benefit of priority from U.S. Provisional Application Ser. Nos. 60/238,479 filed Oct. 6, 2000, and 60/215,779 filed Jul. 5, 2000.

STATEMENT REGARDING FEDERALLY SPONSORED RESEARCH OR DEVELOPMENT

This invention was funded by the National Institutes of Health. The Government has certain rights in the invention pursuant to grant A142549-02.

FIELD OF THE INVENTION

The invention relates to polypeptides and nucleic acids encoding polypeptides that modulate the activity of transcription factors and methods of screening for same.

BACKGROUND OF THE INVENTION

Transcription factors are important regulators of gene expression. Gene-specific transcription factors provide a promising class of targets for novel therapeutics directed to human diseases. For example, transcription factors offer substantial diversity. Over 300 gene-specific transcription factors have been described, and the human genome may encode as many as 3000. Transcription factors also offer substantial specificity. Each and every factor offers unique molecular surfaces to target. Additionally, transcription factors are known to be involved in a wide variety of human diseases. For example, many tumors are associated with the activation of a specific oncogene. A third of known proto-oncogenes and three fourths of all anti-oncogenes are transcription factors. Transcription factors involved in cancers, such as leukemias and lymphomas, include Ets and Stat related transcription factors.

Signal transduction pathways often effect changes in cellular biology by inducing programs of gene expression through the activation of transcription factors. NF-KB is a transcription factor in that it is activated by many diverse stimuli that alert a cell or organism to stressful or infectious conditions and activate a response (Baldwin, A. S., Jr., *Annu Rev Immunol* 14:649–83 (1996); Ghosh, S., et al., *Annu Rev Immunol* 16:225–60 (1998)). These include UV and γ-irradiation, bacterial and viral products (e.g., lipopolysaccaride and dsRNA), proinflammatory cytokines (e.g., TNFα and IL-1), antigen recognition by the T cell and B cell receptor complexes, and apoptotic and necrotic stimuli. NF-KB regulates a multitude of genes involved in the development and function of the immune response, inflammation, cell growth control, and in antiapoptotic responses (Pahl, H. L., *Oncogene* 18:6853–66 (1999)). In addition, several viruses use NF-KB to regulate viral gene expression, including HIV, HSV, EBV, CMV and Adenovirus. Moreover, activiation of this transcription factor contributes to the resistance of some tumors to chemotherapeutic agents.

Many stimuli activate NF-KB by causing the phosphorylation and destruction of IKBS, inhibitory molecules that bind NF-KB in the cytoplasm. The signal-induced phosphorylation of IKB occurs at two specific serines in its N-terminus and is accomplished by the IKK complex, which is composed of two kinase subunits, IKKα and IKKβ, and a noncatalytic subunit, NEMO/IKKγ (Karin, M. & Y. Ben-Neriah, *Annu Rev Immunol* 18:621–63 (2000)). Subsequent to phosphorylation, IKB is ubiquitinated and degraded by the 26S proteasome, leaving NF-KB free to translocate to the nucleus to activate target genes.

Several pathways that activate NF-KB employ a set of signaling molecules that link stimulus recognition to IKK complex activation. These include cell surface receptors which recognize ligands, proximal kinases that may directly phosphorylate and activate the IKK complex, and adapter proteins which physically link ligand-bound receptor complexes to kinase activation. The IKK complex is activated by many stimuli, but the mechanism has not been reported on.

Current methods for the identification of molecules that modulate activity of a transcription factor include yeast two-hybrid screening using a particular bait molecule. The bait molecule is usually a molecule known to modulate activity of the transcription factor. Another method is the biochemical purification of proteins physically associated with a particular molecule known to modulate activity of a transcription factor. These two methods have inefficiencies because they use as the detection method a binding property, i.e. the ability to bind to a particular target molecule which itself is a component of the signaling pathway for activating the transcription factor. Thus, these methods detect proteins which can bind to a particular target molecule, whether or not the detected protein actually participates in regulation of the transcription factor. These methods are also limited by what bait/target molecule is used for detecting associated proteins.

Another current approach to identifying transcription factor modulators is the biochemical purification of proteins which possess specific catalytic properties. These specific catalytic properties have been determined to be critical steps in one or more pathways that modulate activity of a particular transcription factor. This method is limited in that it only detects molecules with specific catalytic functions. For example, if one uses this method to detect and isolate a kinase for IKB (the inhibitor of the transcription factor NF-KB), one would only find kinase molecules by this method.

Yet another current approach is the cloning of genes homologous to molecules known to modulate activity of a transcription factor. This method is limited in that it only detects genes/proteins with particular homology. For example, if one uses this method to detect (by conventional low stringency screening of cDNA libraries) homologs of TRAF2, a known activator of NF-KB, one would only find members of the TRAF family of proteins in the screen.

Therefore, it is desirable to provide new and more efficient methods to identify molecules which participate in signaling pathways involving transcription factors. It is further desirable to identify and provide therapeutic targets for disease states involving altered activity of transcription factors.

SUMMARY OF THE INVENTION

In one aspect, the present invention provides a method for screening for an agent which modulates transcription factor activity which comprises providing a cell comprising a transcription factor of interest and a vector comprising a binding site for said transcription factor of interest operatively linked to a reporter gene. The method further comprises introducing a plurality of candidate agents to said cell, and, determining the activity of said transcription factor. A change in activity between the presence and absence of said candidate agents indicates the presence of an agent which modulates transcription factor activity. The methods may further comprise introducing into said cell a control plasmid comprising a constitutively expressed gene to monitor transfection efficiency.

Agents capable of modulating transcription factor activity and identified by the methods provided herein may be used as targets for the development of therapeutics and prophylactics for the treatment of disease states. In addition, these agents may be used to identify additional molecules involved in the regulation of transcription factor activity, thereby providing additional targets for the development of therapeutics and prophylactics. Moreover, the agents identified by the methods provided herein may themselves be used as therapeutic or prophylactic compounds.

In one embodiment, the plurality of candidate agents is a pool of cDNA clones from an expression library. Provided herein are screening methods that efficiently identify cDNAs which encode signaling molecules that modulate transcription factors. From these methods, cDNAs for molecules that are known components of pathways that activate the transcription factor, as well as molecules that have not been previously linked to the transcription factor have been identified. The identities of cDNAs isolated from the methods provided herein indicate that the provided methods can detect signaling molecules of different biochemical types and can be used to isolate components of multiple signaling pathways. The identified molecules can then be used as targets for the development of therapeutic agents for disease states, including those that involve inflammation and dysregulated or aberrant cell growth.

In another embodiment, the plurality of candidate agents is a pool of genomic DNA clones. Provided herein are methods for screening for genomic DNAs that are capable of modulating the activity of a transcription factor. In a preferred embodiment, the methods comprise providing a cell comprising a transcription factor of interest and a vector comprising a binding site for said transcription factor of interest operatively linked to a reporter gene, and further comprise introducing a plurality of genomic DNAs into the cells and determining the activity of said transcription factor. A change in activity between the presence and absence of the genomic DNAs indicates the presence of a genomic DNA which modulates transcription factor activity.

Genomic DNAs may include prokaryotic and eukaryotic DNAs. In the case of eukaryotic genomic DNAs, the use of eukaryotic cells for screening for modulation of transcription factor activity is preferred.

The reporter gene can be a variety of genes. For example, in one embodiment the reporter is a luciferase gene. In another embodiment the reporter gene encodes a fluorescent protein. In a preferred embodiment, a reporter gene is such that the activity of the reporter gene can be determined by an automated process, such as by fluorescence assay in a luminometer.

The method can be used to report transcription factor activity that is stimulated or inhibited. Preferably, the activity is stimulated or enhanced.

Once the presence of a modulator in a pool has been identified, the pools of candidate agents can be further subdivided and screened for activity until an individual agent is identified.

In one embodiment, a cDNA expression library is subdivided into pools, each of which is assayed for the ability to modulate, for example, activate a transcription factor responsive reporter. Positive pools are assayed in a secondary screen to confirm their dependence on the transcription factor binding sites. Specific pools can then be assayed in the presence of dominant negative variants of known signaling proteins to obtain epistatic or other functional information about a pool's activity. The clone responsible for an interesting pool's activity can then purified by sib selection and sequenced.

The agents which are identified as interacting with the transcription factor to modulate activity can then be further screened if desired. For example, a number of agents have been identified herein as activating NF-KB. These agents include but are not limited to TRAIL, TNFR1, TRAMP, TRAF2, MyD88, IKK-i/ε, rhoB, Snk and MARCKS. Thus, any of these agents can be combined with NF-KB and a candidate agent to determine agents which modulate the interaction between NF-KB and the said agent. In this respect, standard assays for determining binding, for example, can be used.

Other components of the invention will become apparent by the description of the invention which follows.

DETAILED DESCRIPTION OF THE INVENTION

Figure 1:
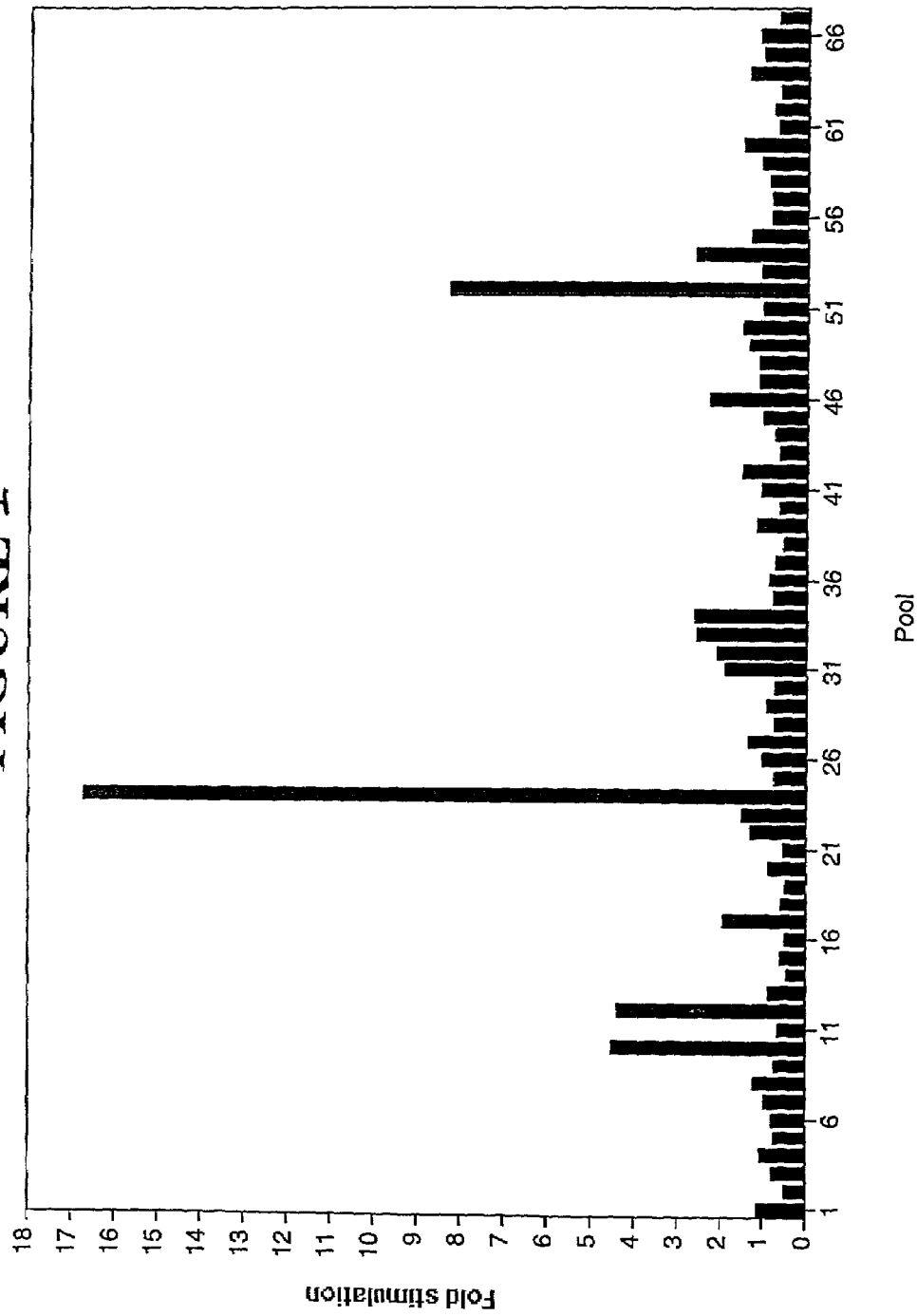
FIG. 1 represents relative expression obtained from transfecting pool DNA into 293T cells with $IgK_2$-IFN-LUC reporter and the pCSK-lacZ control vector.

Methods for the identification of modulators of transcription factors are provided, making possible the characterization of signaling pathways and providing for novel therapeutics. More particularly, the present invention makes possible the identification and characterization of molecules useful in prognosis, diagnosis, monitoring, rational drug design, and/or therapeutic intervention of diseases that involve an altered regulation of a transcription factor.

In one aspect of the invention, a method for screening for an agent which modulates transcription factor activity is provided. The method can be used to identify the presence of such an agent within a pool of candidate agents. In another embodiment, the method is repeated until one candidate agent is identified as a modulator.

In one embodiment, the method of screening comprises providing a cell comprising a transcription factor of interest and a vector comprising a binding site for a transcription factor of interest operatively linked to a reporter gene; introducing a plurality of candidate agents to said cell; and, determining the activity of said transcription factor, wherein a change in activity between the presence and absence of said candidate agents indicates the presence of a candidate agent which modulates transcription factor activity.

The transcription factor of interest can be any transcription factor. Transcription factors are known in the art. For example, transcription factors include the superclass of basic domains which include the class of leucine zipper factors (bZIP), including the family of AP-1(-like) components and the subfamilies of Jun, Fos, Maf, NF-E2, fungal AP-1- like factors, CRE-BP/ATF, Zta and CYS3. bZIP further includes the families of CREB, C/EBP-like factors, and bZIP/PAR. bZIP also includes the family of plant G-box binding factors and subfamilies CRPF-2 ("V"), EmBP-1 ("E"), HBP-1a ("Q"), TGA1a ("L/M"), TGA1b ("R"). bZIP further includes the ZIP only family and other bZIP factors.

The basic domains superclass also includes the class of basic helix-loop-helix factors (bHLH), including the families of ubiquitous (class A) factors, myogenic transcription factors, heamatopoietic transcription factors including SCL, and neurogenic transcription factors including achaete-scute. bHLH also includes the family of tal/twist/atonal/hen and subfamilies lymphoid factors, mesodermal twist-like factors, hen, atonal, and pancreatic factors. bHLH also includes the family of hairy which includes the subfamilies of hairy, E(spl), and fungal regulators bHLH also includes the families of factors with PAS domain, INO, HLH domain only, and other bHLH factors.

The basic domains superclass also includes the class of helix-loop-helix/leucine zipper factors (bHLH-ZIP). bHLH-ZIP includes the family of ubitquitous bHLH-ZIP factors and the subfamilies of TFE3, USF, SREBP and AP-4. bHLH-ZIP includes the family of cell-cycle controlling factors and the subfamilies of myc, mad/max, E2F, and DRTF.

The basic domains superclass further includes the class and family of NF-1. The basic domains superclass further includes the class and family of RF-X. Furthermore, the basic domains superclass includes the class of bHSH and family of AP-2.

Another superclass is the zinc-coordinating DNA-binding domains. One such class is the cys4 zinc finger of nuclear receptor type including the family of steroid hormone receptors and subfamilies of corticosteroid receptors, progesterone receptors, androgen receptors, and estrogen receptors. Another family is the thyroid hormone receptor-like factors and the subfamilies of retinoic acid receptors, retinoid X receptors, thryroid hormone receptors, vitamin D receptor, NGFI-B, FTZ-F1, PPAR, EcR, ROR, T11/COUP, HNF-4, CF1, and knirps.

The zinc-coordinating DNA binding domains superclass further includes the class of diverse cys4 zinc fingers which includes the family of GATA-factors and the subfamilies of vertebral GATA-factors and fungal metabolic regulators. Another family of this class is the trithorax family.

The zinc-coordinating DNA binding domains superclass further includes the class of cys2his2 zinc finger domain which includes the family of ubiquitous factors, and the family of developmental/cell cycle regulators including the subfamilies of Egr/Krox, kruppel-like, GLI-like, and others. Other families of this class are the metabolic regulators in fungi, large factors with NF-6B-like binding properties, and viral regulators.

The zinc-coordinating DNA-binding domain superclass further includes the class of cys6 cysteine-zinc cluster and the families of metabolic regulators in fungi.

The zinc-coordinating DNA-binding domain superclass further includes the class of zinc fingers of alternating composition and the families of Cx7Hx8Cx4C zinc fingers, and Cx2Hx4Hx4C zinc fingers.

Another superclass is the helix-turn-helix. This superclass includes the class of homeo domain and the family of homeo domain only which includes the subfamilies of AbdB, Antp, cad, cut, dl, ems, en, eve, prd, hd-zip, h2.0, HNF1, Lab, Msh, NK-2, Bcd, XANF, PBC, and other unassigned subfamilies. Another family of this class includes POU domain factors which include the subfamilies II, III, IV, V, VI, and other POU factors. Another family is the homeo domain with LIM region which includes the subfamilies of homeo domain with LIM region and the subfamily of LIML-only transcription (co-) factors. Moreover, this class includes the family of homeo domain plus zinc finger motifs.

Another class of the helix-turn-helix superclass is the paired box which includes the families of paired plus homeo domain and paired domain only. A further class is the fork head/winged helix which includes the families of developmental regulators, tissue-specific regulators, and other regulators.

Yet another class of the helix-turn-helix (HTH) superclass is the heat shock factors. This class includes the family of HSF. Furthermore, another class is the tryptophan clusters which includes the family of myb and the subfamily of myb-factors. Other families of this class are the Ets-type and the interferon-regulating factors. Yet another class is the TEA domain class including the family of TEA.

Another superclass includes the beta-scaffold factors with minor groove contacts which include the class of RHR (rel homology region) which includes the families of rel/ankyrin, ankyrin only and NF-AT.

Another class is STAT which includes the family of STAT. Yet another class and family is that of p53.

Another class is the MADS box having the family of regulators of differentiation, and the subfamilies of MEF-2, homeotic genes, and yeast regulators. Other families of this class are the responders to external signals and metabolic regulators. Yet another class of this superclass is the beta-barrel alpha-helix transcription factors including the family of E2. Another class is that of the TATA-binding proteins which include the family of TBP. Another class is the HMG, including the families of SOX, TCF-1, HMG2-related, UBF, MATA, and other HMG box factors.

The superclass of beta-scaffold factors with minor groove contacts further includes the class of heteromeric CCAAT factors which includes the family of heteromeric CCAAT factors. Another class and family is that of grainyhead. A further class is the cold-shock domain factors which include the family of csd and the subfamilies A (Dbp A-like), B (YB-1/DbpB-like), and C (FRG Y2-like). Yet another class and family is that of runt which includes the subfamilies PEBP2alphaA, B and C, and lozange.

Moreover, there are other classes and families which are not in the above superclasses. Such classes include copper fist proteins which include the family of fungal regulators, the class and family of HMGI(Y). The class of pocket domain which includes the families Rb and CBP. Yet another class is the E1A-like factors including the E1A family. A further class is the AP2/EREBP-related factors including the AP2, EREBP and AP2/B3 families.

As should be understood, the list of transcription factors is known to the artisan. The members of each class and subclass are specifically incorporated by reference. Binding sites for transcription factors are well known in the art. A database of transcription factors is available though TRANSFAC—The Transcription Factor Database. Preferred transcription factors include NF-KB, ETS, STAT, p53, Ap-1 family, steroid hormone and related families. In a preferred embodiment, NF-kB binding sites are used. A variety of sites can be used including the consensus site 5'GGGRNYYYCC3' described in Chen and Ghosh, Oncogene 1999, 18:6845–6852.

In a preferred embodiment, the cell that is used in the methods provided herein is one which endogenously expresses the transcription factor of interest. If the cell endogenously expresses the transcription factor, more information is generally obtained in the screening process. Therefore, while it is understood that any cell can be used to determine whether activity is modulated by the methods provided herein, use of a cell endogenously expressing said transcription factor is preferred. Thus, while in one embodiment, prokaryotes or eukaryotes can be used, preferred embodiments utilize eukaryote cells, preferably mammalian or plant cells. While the cell may or may not endogenously express the transcription factor, the cell can be engineered to express the transcription factor using standard recombinant techniques. For example, while the cell may endogenously express the transcription factor, it may be desirable to have the transcription factor under the control of an inducible plasmid, etc.

The use of recombinant techniques to engineer a cell that expresses a gene encoding a transcription factor of interest may be particularly desirable when a cell type normally expressing the transcription factor of interest is difficult to maintain in culture. Additionally, the transcription factor of interest may normally be expressed in cells in a restricted developmental window or stage that is difficult to maintain in culture. Additionally, the effects of transcription factor activity increase or decrease may be detrimental to a native cellular context, requiring the use of an alternative cell type and/or control over the level of expression. Additionally, it may be desirable to perform the screen in a modified genetic background that requires recombinant engineering of a cell to express the transcription factor of interest at a desirable level in such a background.

Primary cells or cell lines can be used. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). In a preferred embodiment, 293T cells are used. These cells stably express the SV40 large T antigen, which leads to higher levels of expression of cDNAs transfected into the cell. The selection of the appropriate host cell is deemed to be within the skill in the art.

It will be understood that in a preferred embodiment, where it is desirable that screens for modulators of transcription factor activity use a transcription factor of interest in its endogenous cellular context, that the spatiotemporal pattern of expression of the gene encoding the transcription factor will be instructive as to the type of cell that may be used in the method.

The cell in said method provided comprises a vector comprising a binding site for the transcription factor of interest. The cell can be transformed or transfected with said vector using standard techniques in the art (for example, see Sambrook et al., Molecular Cloning: A Laboratory Manual, $2^{nd}$ Edition, Cold Spring Harbor, N.Y., 1989). In one aspect of the invention, the cell further comprises a reporter system which detects transcription activity. In a preferred embodiment, the vector comprising a binding site for the transcription factor of interest is operatively linked to a reporter gene.

It will be appreciated that a transcriptional activity need not be provided by a single protein. For example, a DNA binding protein and a transcriptional regulatory protein lacking intrinsic DNA binding activity (for example a component that interacts with the RNA POL II directly or indirectly to influence the rate of transcription initiation but does not bind DNA) may interact to regulate transcription from a particular DNA binding site. The present invention provides methods that may be used to screen for modulators of such multi-component transcriptional activity.

In addition it will be appreciated that while the use of transcription factors for which DNA binding sites are known is preferred, methods are known in the art for determining the DNA binding sites of transcription factors. For example, chemical crosslinking of protein to DNA or DNA footprinting may be used to determine DNA binding sites for transcription factors.

A reporter gene is any gene for which the level of expression can be specifically determined. Preferably, a reporter gene encodes a protein product possessing an activity that is readily determinable and quantitatable by conventional means known in the art. Reporter genes are known in the art. In a preferred embodiment, the reporter gene is the luciferase gene. The luciferase gene allows quantification of its expression by use of a luminometer. Other examples of reporter genes include chloramphenicol acetyl transferase (CAT), green fluorescent protein (GFP), β-galactosidase, human growth hormone (hGH), secreted alkaline phosphatase (SEAP), β-glucuronidase. In an alternative embodiment, drug-selectable genes can be used, including those that impart resistance to hygromycin, neomycin, puromycin, and zeocin. In an additional embodiment, any gene can be used if the assay involves detecting mRNA by Northern blot, Rnase protection, RT-PCR, or any other known method.

In a further aspect of the invention, a plurality of candidate agents is introduced to said cell. A change in the activity of said transcription factor between the presence and absence of said candidate agents indicates the presence of a candidate agent which modulates transcription factor activity. As indicated above, one or more candidate agents may be used. Wherein a plurality of candidate agents are used, one may, as desired, divide the candidate agents into further subpopulations and perform a series of screens until one candidate agent is identified as a modulator of transcription factor activity.

In a preferred method, the activity of the transcription factor is determined by the measuring or determining the detection of the reporter gene. Generally, if the transcription factor of interest either directly or indirectly binds to the binding site of interest, the reporter will detect such activity.

A modulator/candidate agent may also act on the transcription factor once the transcription factor is already bound to its DNA binding site. For example, a transcription factor might be bound to its DNA site and yet be inactive, and the introduced agent might lead to a conformational change, covalent modification such as phosphorylation, non-covalent modification such as association with an auxiliary factor, or other modification of the transcription factor, causing it to become active. A difference in the activity in the presence and absence of a candidate agent(s) will indicate the presence of a modulator. It is understood that the candidate agent does not necessarily need to be absent, rather, a control must be set which the test candidate is measured against. The change is any detectable change, but generally at least about 20%, more preferably about 50%, more preferably about 100% or more.

Modulation of the activity of transcription factors includes stimulation, enhanced time of stimulation and inhibition. For development of new therapeutics, the altered expression/activity of the transcription factor of interest is determined. If the transcription factor activity is reduced in the disease state, then agents which stimulate transcription factor activity are desirable and are screened for. If the transcription factor activity is enhanced in the disease state, then agents which decrease or inhibit transcription factor activity are desirable and are screened for.

In one aspect of the invention, the activity of the transcription factor as used herein is dependent on the activation of transcription factor binding to its cognate binding site. However, the present invention provides for identifying the modulation of transcription factor activity at several levels. For example, transcriptional activity may be modulated by altering synthesis of the transcription factor at the transcription or translation level, or altering cellular localization of the transcription factor by posttranslational modification, e.g. phosphorylation, or altering association of the transcription factor with co-factors such as by the alteration of co-factor synthesis, activity, or localization, or by altering the presence of or association with an inhibitor or inducer of the transcription factor. Further, transcription factor activity can be modulated by modification of the transcription factor while bound to its binding site.

In a preferred embodiment, the candidate agent is a nucleic acid encoding a polypeptide that modulates transcription factor activity. In the broadest sense, by "nucleic acid" is meant at least two nucleotides covalently linked together. In a preferred embodiment, the nucleic acid of the invention is a gene. Gene in this context includes full length genes and fragments thereof, and can comprise the coding strand, its complement, or both, and can be a portion of a gene, a regulatory sequence, genomic DNA, cDNA, RNA including pre-spliced RNA, mRNA and rRNA, etc. In the present invention, such a gene encodes a polypeptide. In a preferred embodiment, such a gene encodes a full length protein. However, many desirable modulators may be discovered that are shorter polypeptides, possibly truncated from the full length protein. Candidate nucleic acids may be derived from a single nucleic acid of unknown sequence which encodes a polypeptide, a small number of nucleic acids, for example, several ESTs, or larger number of sequences. The nucleic acids may be naturally occuring or libraries of variants. In a preferred embodiment, large number of sequences are screened as a pool of expression vectors comprising nucleic acids operably linked to regulatory sequences for expression of the peptides encoded thereby. In a preferred embodiment, a large number of sequences are screened as a pool of cDNAs.

In a preferred embodiment, a cDNA library is cloned into an expression vector, preferably a mammalian expression vector and divided into pools of clones. The cDNA expression library is screened in pools. Positive pools are further subdivided and screened in a process known as sib selection. In a preferred embodiment, each initial pool has approximately 100 clones. However, in other systems, pool size may range, for example, from about 50 clones to a pool size of several thousand. To maximize the number of cDNAs that could be assayed in a transfection, the complexity is determined (i.e. number of cDNAs per pool) that will allow reliable detection of a single active clone in a mixture of cDNAs. This will be dependent upon the background and induced activities of the transcription factor of interest. Other criteria include the choice of cell type, cDNA library source tissue and choice of reporter gene.

The optimal pool complexity can be determined empirically or through pilot experiments. An empirical determination divides a subset of the pool into pools of different complexity. For a pilot experiment, proteins in the signaling pathway of interest can be chosen and the desired level of specific activity examined. For example, for NF-KB, TRAF2 is an adaptor protein in the TNFα pathway (Rothe, M. et al., Science 269:1424–7 (1995)). To allow detection of molecules possessing three-fold lower specific activity than TRAF2 in one system, it was determined that the optimal pool complexity was 100 cDNAs.

Alternatively, it may be desirable to screen entire libraries with different pool complexities. Due to variations in expressed proteins, e.g. specific activity, some proteins may only detectable within a certain pool complexity range.

Each pool is assayed for the ability to activate a transcription factor-dependent reporter in a transient transfection assay in tissue culture cells. Pools with the desired regulatory activity (either stimulatory or inhibitory) are further subdivided and screened until a single cDNA is isolated with the desired activity. As a control, positive pools are screened for the ability to regulate a mutant version of the reporter, in which the NF-KB binding sites have been mutated. Positive pools which do not regulate the mutant reporter are determined to be specific. In a preferred embodiment, the NF-KB-responsive promoter has two copies of the KB site (5' GGGGACTTTCC-3' (SEQ ID NO 2)). The mutant reporter is identical except that the two NF-KB sites have been mutated to (5'-ATCCACTTTCC-3' (SEQ ID NO:3),. Eventually, a single cDNA is obtained which will encode a gene product that can regulate the activity of the transcription factor of study. This individual clone is then sequenced to identify the cDNA it contains and the gene product it expresses.

A secondary screen is desirable to assess dependence on a particular binding site for activity and also to measure and compare the effects of contransfected molecules like dominant negatives. In principle, any dominant negative molecule could be used to target the discovery of cDNAs encoding components of a particular pathway, or components that function at a particular epistatic level of a pathway. Other uses for secondary screens are envisioned. For example, pools can be screened for the ability to synergistically activate the reporter with a particular cotransfected molecule or with an applied stimulus.

Any method may be used to prepare a cDNA library from a cell that expresses the desired protein. In one method, the cDNA library is prepared by extracting the mRNA from a culture of cells that express the desired protein, using known methods, for example, isolation of polyadenylated (poly $A^+$) RNA. Kits for isolating poly $A^+$ RNA are commercially available, for example, the PolyATract™ is available from Promega Corporation (cat. #Z5420). The cDNAs corresponding to the mRNAs are prepared using a reverse transcriptase for first strand synthesis and a DNA polymerase for second strand synthesis. Methods for using reverse transcriptase and DNA polymerase to make cDNA are well known in the art. Kits for performing these techniques are commercially available, for example, the Superscript II™ kit (Gibco-BRL, Gaithersburg, Md., U.S.A., cat. #18248-013), the Great Lengths cDNA Synthesis Kit™ (Clontech, Palo Alto, Calif., U.S.A., cat. #K-1048-1), the cDNA Synthesis Kit (Stratagene, La Jolla, Calif., U.S.A., cat. #200401), and the like. The cDNAs may then be ligated to linker DNA sequences containing suitable restriction enzyme recognition sites. Such linker DNAs are commercially available, for example, from Promega Corporation, Madison, Wis., U.S.A. and from New England Biolabs, Beverly, Mass., U.S.A., and the particular linker used may be selected to conform to the protocol being used. The cDNAs may be subjected to restriction enzyme digestion, size fractionation, or any other suitable method, to enrich for full-length cDNAs within the library. Alternatively, a commercially available cDNA library such as the Human Brain Library (Clontech, Palo Alto, Calif., U.S.A., cat. #HL3002S), the Human Liver Library (Clontech, Palo Alto, Calif., U.S.A., cat. #HL3006S), and the like may be used in the method of the invention. In this case, polyadenylated mRNA was derived from human placenta, reverse transcribed and cloned directionally into an expression vector which uses the CMV promoter to express the cDNA. The library was manufactured by and purchased from Origene Technologies, Inc., Rockville, Md.

The nucleic acids are inserted into an expression vector which contains sequences that direct DNA replication in a cell and which also contains sequences that direct DNA transcription and mRNA translation. This insertion step may optionally be performed in such a way that the nucleic acids are inserted into the expression vector in a preferred direction. Any expression vector capable of directing DNA replication in a cell and of directing DNA transcription, and mRNA translation may be used in practicing the method of the invention. Many such vectors are commercially available. Construction of expression vectors is within the level of ordinary skill in molecular biology, as indicated in U.S. Pat. No. 4,675,285, as is construction of expression vectors containing DNA sequences which direct transcription and translation. Generally, these expression vectors include transcriptional and translational regulatory nucleic acid operably linked to the nucleic acid encoding a differentially expressed protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and/or enhancer sequences.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used. Numerous types of appropriate expression vectors, and suitable regulatory sequences are known in the art for a variety of host cells.

Promoter sequences encode either constitutive or inducible promoters. The promoters may be either naturally occurring promoters or hybrid promoters. Hybrid promoters, which combine elements of more than one promoter, are also known in the art. Enhancers may also be either naturally occurring or hybrid enhancers.

In addition, the expression vector may comprise additional elements. For example, the expression vector may have two replication systems, thus allowing it to be maintained in two organisms, for example in mammalian or insect cells for expression and in a procaryotic host for cloning and amplification. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art. The expression vector may also contain a selectable marker gene to allow the selection of transformed host cells. Selection genes are well known in the art and will vary with the host cell used. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

In a preferred embodiment, the polypeptides are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for differentially expressed protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

A reporter vector or plasmid is constructed from an expression vector so that sites for binding the transcription factor of interest are present such that they regulate expression of a reporter gene. Applicable host and viral or microbial transcription factors and corresponding oligonucleotide targets are found in sources such as the regularly updated Transcription Factor Database of the National Center for Biotechnology Information at the National Library for Medicine and Faisst and Meyer (1991) Nucleic Acids Research 20, 3–26; see also Svetlov et al., Yeast, 11:1439–1484, 1995; Boulikas, Crit. Rev. Eukaryot. Gene Expr. 4:117–321, 1994; Wingender, Nucleic Acids Res. 16:1879–1902, 1988. These binding sites can be obtained from known gene sequences in commercially available plasmids or synthesized as oligonucleotides, both as known in the art. The reporter gene is engineered to be controlled by the activity of the transcription factor of interest by placing DNA binding sites for the transcription factor into the cis-regulatory regions of the reporter gene (promoter or enhancer). Thus, changes in activity of the reporter gene reflect changes in the transcriptional activity of the transcription factor of study. In an embodiment of the present invention, two NF-KB binding sites (from the kappa enhancer) upstream of the minimal promoter for the interferon beta gene were cloned into the reporter plasmid.

It may also be desirable to use more than one type of binding site within the regulatory region. For example, to find modulators of expression of a particular gene, it would be possible to include the complete promoter sequence with binding sites to different transcription factors.

In a preferred embodiment, a reporter gene may be "knocked in" to a desired nucleic acid sequence within the genome of a cell. For example, a reporter gene may be "knocked in" at a particular chromosomal location such that it is operably linked to an endogenous regulatory sequence that is modulated by a transcriptional activity of interest. Operable linkage may be achieved by replacing endogenous coding sequence of a gene with the reporter gene. Preferably, disruption of te endogenous gene does not have detrimental effects for the cell being used.

In one embodiment, a control plasmid is further used to measure the transfection efficiency and cell extract recovery. Such a plasmid is also designed to express a gene, but it is constitutively expressed to provide a comparison to other cells. Expression of this control plasmid is not dependent upon modulation of the activity of the transcription factor of interest. In an preferred embodiment, quantification of the expression of the reporter gene and the control gene is measured using the same assay, but with different parameters. In a preferred embodiment, the control plasmid constitutively expresses β-galactosidase activity. β-gal activity is detected in a conventional assay, also using a luminometer.

A preferred host-vector system for the isolation of a clone containing DNA coding for a mammalian protein or factor is based on transient expression of the cDNA by a suitable vector in mammalian cells.

The methods of introducing nucleic acids into mammalian hosts, as well as other hosts, is well known in the art. The culture conditions, such as media, temperature, pH and the like, can be selected by the skilled artisan without undue experimentation. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. Depending on the host cell used, transformation is performed using standard techniques appropriate to such cells. The calcium treatment employing calcium chloride, as described in Sambrook et al., supra, or electroporation is generally used for prokaryotes. For mammalian cells without such cell walls, the calcium phosphate precipitation method of Graham and van der Eb, *Virology,* 52:456–457 (1978) can be employed. General aspects of mammalian cell host system transfections have been described in U.S. Pat. No. 4,399,216. For various techniques for transforming mammalian cells, see Keown et al., *Methods in Enzymology,* 185:527–537 (1990) and Mansour et al., *Nature,* 336:348–352 (1988).

Not all the plasmids need to be transiently transfected. For example; the control plasmid or reporter plasmid may be stably transfected into the host cell.

In general, in preferred embodiment of the invention, prokaryotes are used for the preparation of plasmid DNA, including preparing pools of cDNA. Mammalian cell lines are used for screening, in particular, for the expression of candidate nucleic acids and the reporter gene.

In a preferred embodiment of the invention, expression of the reporter gene is measured by chemiluminescence. FACS and other methods may also be used. Expression of a reporter gene is said to report activity of the transcription factor. Other means of measuring gene expression may be employed. A change in expression is any detectable change. This includes both quantitative and qualitative changes. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference.

In a preferred embodiment of the invention, the method of screening uses a functional assay. In the present invention, it is the ability to directly modulate the activity of endogenous transcription factors in expression of a gene. As discussed above, this will detect any molecule which can regulate the activity of the transcription factor, regardless of what proteins it may need to associate with the function, regardless of what catalytic or non-catalytic properties it may employ to activate the transcription factor, and regardless of whether that molecule has any homology to any known protein.

Once a single clone is found that modulates the activity of the transcription factor of interest, the desired cDNA is excised from the clones by restriction enzymes and can be sequenced by known techniques. It can be readily appreciated that the procedure described herein can be used to obtain cDNA clones from any source as long as the expression product can be detected. Moreover, the polypeptide encoded by the nucleic acid can be obtained.

As desired, the identified nucleic acids and polypeptides may be further manipulated, for example mutated, to determine whether their mutation causes further modulation of said transcription factor. In a preferred embodiment, the identified nucleic acids and polypeptides which are modulated are used in further screens such as two-hybrid screens to identify new modulators of said identified modulators.

For studying signaling pathways, the present invention can be used to look for cDNAs which encode proteins in particular pathways or at particular levels of pathways, i.e., characterized by the ability to be inhibited by particular dominant negatives. Further, cDNAs which encode proteins which inhibit transcription factor activation by any particular stimulus can be looked for. These would include 1) natural inhibitory proteins and 2) cDNA fragments of genes which normally function to activate but which would behave as inhibitory because they express only partial gene products that might poison the signaling pathway (dominant negatives).

For the development of new therapeutics, once the nucleic acid encoding a modulator of transcription factor is isolated, new drugs can be investigated using methods and techniques known in the art. These include antisense approaches, monoclonal antibodies, and chemical designs. Chemical agents can be produced and screened using combinatorial chemistry approaches, molecular modeling/rational drug design approaches or any other method known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein and sequences referred to are expressly incorporated by reference in their entirety.

EXAMPLES

Example 1

For illustrative purposes, we have targeted molecules that regulate the transcription factor NF-KB. The invention is easily adaptable to target molecules that regulate any transcription factor for which the DNA binding site is known or can be determined.

NF-KB is a transcription factor that regulates the expression of genes involved in inflammation, in the development and functioning of the immune system and in anti-apoptotic responses. The activation of NF-KB is thus critical for both physiological and pathological inflammatory states, for the normal functioning of the immune system, and it also contributes to the resistance of some tumors to chemotherapeutic agents. The identification of proteins that function to activate NF-KB will provide targets for the development of novel therapeutics for inflammation, cancer and other disease states which depend upon NF-KB-regulated genes.

Construction of an Expression Library

The pools of expression constructs are derived from a cDNA library that has been cloned into a mammalian expression vector. Plasmid DNA from sixteen wells of an arrayed human placenta cDNA library (Origene Technologies, Inc., Rockville, Md.) was used to transform *E. coli* strain DH10B and plated on LB agar (w/100 µg/ml ampicillin) so as to obtain ~100 colonies per agar plate. Colonies were scraped off the plate and a fraction of the pooled bacteria was stored as a 50% (w/v) glycerol stock at –80° C. Plasmid DNA was prepared from the remainder of the bacterial prep by the Qiagen Spin or QIAprep 8 Miniprep kits (Qiagen, Valencia, Calif.) according to the manufacturer's protocol. The cDNAs in this expression library have been primed with oligo(dT), size fractionated and directionally cloned into pCMV6-XL3, which transcribes the cDNA under the control of the CMV promoter and contains an SV40 origin of replication.

Selection of a Reporter Plasmid

The reporter plasmid contains the luciferase gene, the expression of which is driven by two NF-KB binding sites (from the kappa enhancer) upstream of the minimal promoter for the interferon beta gene. NF-KB activation is detected as the increased expression of the luciferase gene which is detected in a conventional assay for luciferase activity using a luminometer.

Screening of a cDNA Expression Library for Activation of NF-KB

For the identification of cDNAs that activate NF-KB, a cDNA expression library (of complexity ≧500,000 different clones) is divided up into pools of clones (of complexity ~100 clones/pool). Each pool is assayed for the ability to activate an NF-KB-dependent reporter in a transient transfection assay in tissue culture cells. Once a pool of cDNA expression plasmids is identified as "positive," (i.e., it activates NF-KB when transfected), the pool is divided up yet again and screened so as to identify and isolate the individual cDNA clone that is responsible for the activity of the pool. This individual clone is then sequenced to identify the cDNA it contains and the gene product it expresses.

The assay for NF-KB activation consists of transfecting tissue culture cells (in this case 293T cells) a reporter plasmid that is used to detect NF-KB transcriptional activation activity, 2) a control plasmid that is used for normalization for transfection efficiency and cell extract recovery, and 3) a pool of expression constructs from the cDNA library to be assayed for the presence of a gene which, when expressed, will activate NF-KB and lead to increased reporter plasmid expression.

293T cells were maintained in DME supplemented with 10% fetal calf serum. 100 U/ml of penicillin and streptomycin, and 2 mM glutamine in humidified 5% $CO_2$ at 37° C. Cells were plated at $9 \times 10^4$/well in 24-well dishes 24 hr before transfection by the calcium phosphate method. A total of 372 ng of DNA was transfected, including 2 ng of pCSK-LacZ, 20 ng of the $IgK_2$-IFN-LUC reporter, and 350 ng of pool DNA. The $IgK_2$-IFN-LUC reporter contains two copies of the $IgK_2$KB site (5'-GGGGACTTTCC-3' (SEQ ID NO:2)) upstream of the interferon-β minimal reporter (–55 to +19) driving luciferase expression (Fujita, T. et al., Cell 49:357–67 (1987)). pCSK-lacZ vector constitutively expresses β-galactosidase and is unaffected by NF-KB activity.

A reference control transfection contained 350 ng pcDNA3 instead of pool DNA. The medium was changed 20–24 hr following transfection, and 40–48 hr following transfection, cells were lysed in 100 µl of reporter lysis buffer (Promega, Madison, Wis.) at room temperature. Cells were scraped off the dish and spun at 13,000 r.p.m. at room temperature for 5 min to pellet cell debris. A 20 µl aliquot of extract was used to measure luciferase activity using the Luciferase Assay System (Promega) and a luminometer (Optocomp I, MGM Instruments, Inc., Hamden, Conn.) integrating for 10 s after a 3 s delay according to the manufacturer's instructions. β-galactosidase activity was determined using 30 µl of extract and the chemiluminescent β-Gal Reporter Gene Assay (Roche Diagnostics, Indianapolis, Ind.) according to the manufacturer's instructions. Fold stimulation was calculated for each sample by dividing the luciferase activity, normalized to β-gal activity, to that observed in the pcDNA3 reference control sample.

Pools were considered positive if they activated the reporter 3 fold or more, relative to the activity observed with the empty expression plasmid pcDNA3. Some pools were considered positive if they displayed 3 fold or greater activity than the average activity of a cohort of pools assayed in parallel. Positive pools were reassayed for confirmation. An example of a primary screening is shown in FIG. 1, in which 67 pools were assayed.

A secondary screen was performed to determine specificity. Positive pool DNA was transfected and assayed as described above except that the MUT-IFN-LUC reporter was used instead of the $IgK_2$-IFN-LUC reporter. Positive pools were considered specific if their activity on the MUT-IFN-LUC reporter was ≦30% of the activity observed on the $IgK_2$-IFN-LUC reporter or if they stimulated the MUT-IFN-LUC reporter <1.5 fold. To examine which specific activities might function upstream of the IKK complex, kinase-dead negative mutants were used. Positive pool DNA was transfected and assayed as described above except that transfections included 75 ng of either pRK-IKKβ K44A (Woronicz, J. D., et al., Science 278:866–9 (1997)) or pc-TBK1 K38A (Pomerantz, J. L. & Baltimore, D., EMBO J. 18:6694–704 (1999)).

A fraction of the bacterial glycerol stock of a positive pool was plated on LB-agar ampicillin and colonies were inoculated into 1 ml LB-amp cultures grown in 24 well plates. Each 24 well plate was treated as a subpool; aliquots of each well culture were pooled and assayed in a single transfection per subpool as in the primary screen described above. Once a subpool was identified as positive, new aliquots were pooled as rows, columns, and levels in a conceptual 4×3×2 matrix, for a total of 9 matrix pools. DNA was prepared from each matrix pool and assayed, unambiguously yielding the coordinates of the well culture containing the cDNA clone responsible for the subpool's activity. DNA from the appropriate well culture was prepared and sequenced with an automated sequencer (Applied Biosystems) so as to obtain sequence at both the 5' and 3' ends of the cDNA insert.

Results

For efficient and economical expression screening a reporter assay for NF-KB activation that is quantitative and highly sensitive was employed. In this assay pool DNA was transiently transfected into 293T cells with the IgK$_2$-IFN-LUC reporter, which contains two copies of the IgK KB site (5'-GGGGACTTTCC-3' (SEQ ID NO:2)) upstream of the interferon-β minimal promoter (−55 to +19) (Fujita. T. et al. Cell 49:357–67 (1987)) driving luciferase expression. For normalization for transfection efficiency and extract recovery, the transfection includes the pCSK-lacZ vector (Condie, B. G., et al., Mol Cell Biol 10:3376–85 (1990)) which constitutively expresses β-galactosidase and is unaffected by NF-KB activity. To maximize the number of cDNAs that could be assayed in a transfection, the complexity was determined (number of cDNAs per pool) which would allow reliable detection of a single active clone in a mixture of cDNAs. Pilot experiments using TRAF2, an adapter protein in the TNFα pathway (Rothe, M., et al., Science 269:1424–7 (1995)), suggested that a pool complexity of 100 cDNAs would allow detection of molecules possessing 3-fold lower specific activity than TRAF2 in this assay (data not shown). The sensitivity of detection of luciferase and β-galactosidase activities allowed us to scale down the size of the transfection and to minimize the amount of pool DNA required.

A portion of an arrayed human placenta cDNA expression library was subdivided into 561 pools of ~100 cDNA complexity. Plasmid DNA from each pool was assayed and pools were considered positive if they activated the reporter 3-fold or more, relative to the activity observed with the empty expression plasmid pcDNA3. In addition, some pools were considered positive if they displayed 3-fold or greater activity than the average activity of a cohort of pools assayed in parallel. Positive pools were reassayed and their ability to activate the IgK$_2$-IFN-LUC reporter confirmed. Of the 561 pools assayed in this way, 41 were positive by these criteria, ranging in fold activation from 2.3 fold to 256 fold. In an example of primary screening which included: providing a cDNA expression library, subdividing into pools, identifying positive pools (e.g., transient transfection with KB-dependent reporter), confirming specificity test with mutated reporter, testing in secondary screen (e.g., inhibition by IKKβ K44A, inhibition by TBK1 K38A) and purifying clone (e.g., divide into subpools, clone identification matrix); 67 pools were assayed and those considered positive were pools 10 (4.5-fold), 12 (4.4-fold), 24 (16.7-fold), and 52 (8.3-fold).

Figure 2:
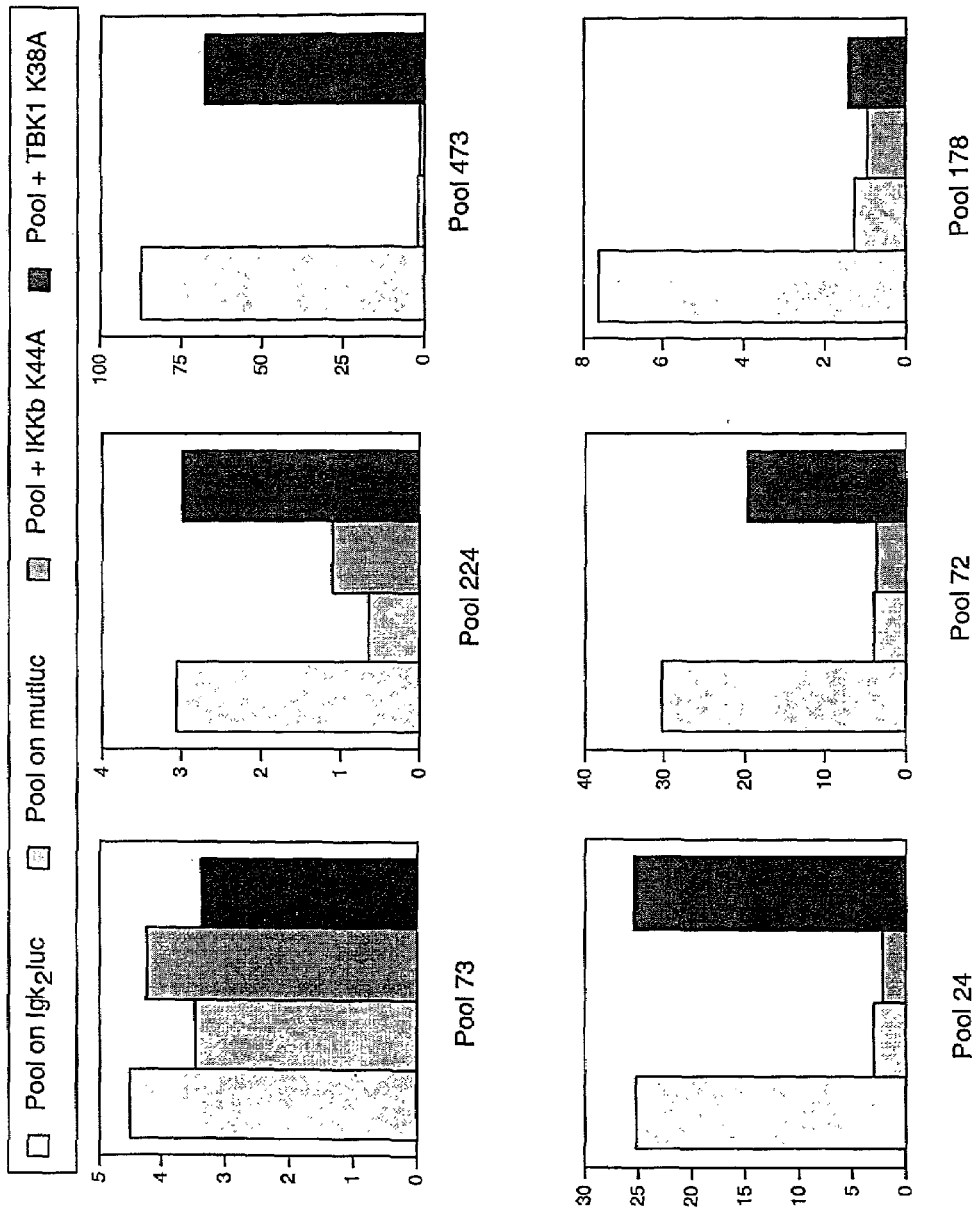
FIG. 2 represents relative expression obtained from transfecting positive pools into 293T cells and assaying the ability to stimulate $IgK_2$-IFN-LUC reporter, the MUT-IFN-LUC promoter, or stimulate $IgK_2$-IFN-LUC reporter in the presence of IKKβ K44A or TBK K38A.

Three secondary screens were applied. First, the NF-KB dependence of a pool's activity was tested by comparing its fold induction on the IgK$_2$-IFN-LUC reporter to that on the MUT-IFN-LUC reporter, which contains mutations in the IgK KB motifs (5'-ATCCACTTTCC-3' (SEQ ID NO:3)). Second, the specific activities which might function upstream of the IKK complex were tested by assessing their activity in the presence of the IKKβ K44A kinase-dead dominant negative. Third, each KB-specific positive pool was tested in the presence of kinase dead TBK1 (K38A), an IKK-related kinase which we recently identified (Pomerantz, J. L. & D. Baltimore. Embo J 18:6694–704 (1999)) (see also (Tojima. Y. et al., Nature 404:778–82 (2000))). Examples of these secondary screens are shown in FIG. 2. Of the 41 positive pools, 34 were found to be dependent on the KB sites for activity. Each of these specific pools was found to be inhibited by cotransfection with the IKKβ K44A. and one pool (pool 178) was also inhibited by cotransfection with TBK1 K38A (FIG. 2).

Figure 3:
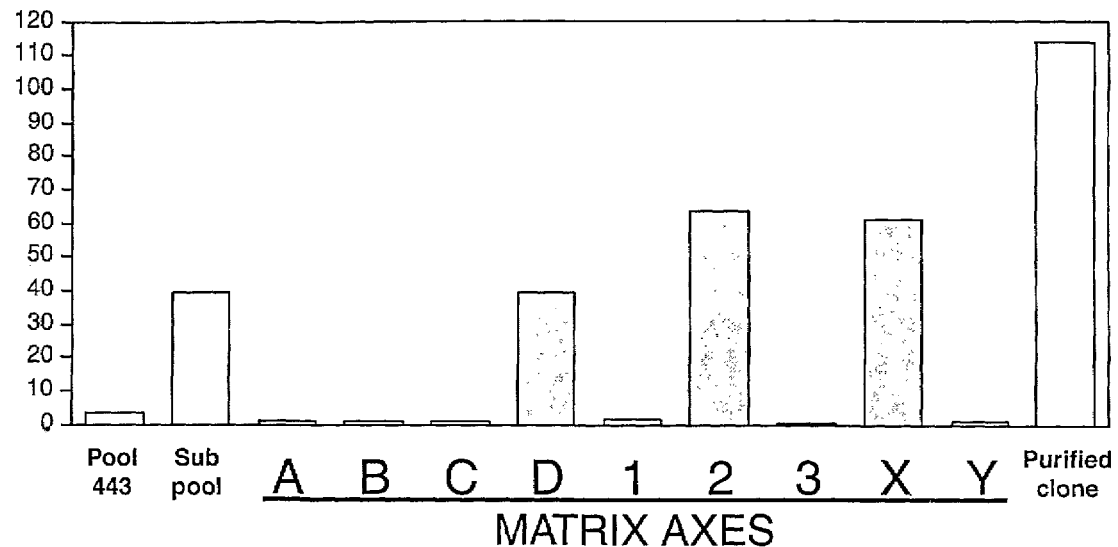
FIG. 3 represents the isolation of a single clone from a pool. The coordinates of the positive well are D2X. A schematic representation of the matrix is also shown.
Figure 3:
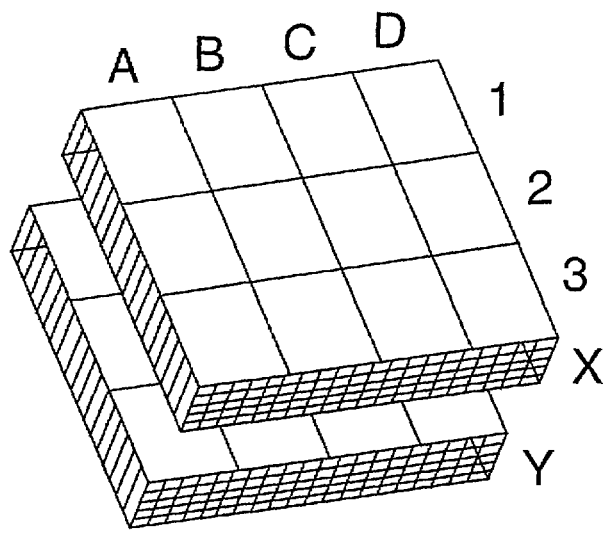

To identify the cDNA responsible for a pool's activity, colonies derived from the glycerol stock of a pool were sib selected. For most pools, the activity increased as the clone was purified, although the activity of some reached saturation in the assay before complete purification. An example of clone purification is shown in FIG. 3, which illustrates the purification of the activity from Pool 443.

The identifies of 23 specific clones are presented in Table I with the representative behavior of pools in primary and secondary screens, and their activities when purified. Eleven of the 23 purified KB-specific clones represented 6 molecules that had been previously linked to pathways known to activate NF-KB. These include the ligand TRAIL, the TRAMP/DR3 and TNFR1 cell surface receptors, the TRAF2 and MyD88 adapter proteins, and IKK-i/ε, an intracellular kinase. TRAIL is a ligand in the TNF family of ligands and functions to regulate apoptosis in the immune system (Pitti, R. M., et al., J Biol Chem 271:12687–90 (1996); Wiley, S. R., et al., Immunity 3:673–82 (1995)). TRAMP and TNFR1 are two death-domain containing members of the large TNF receptor family that function in the immune and inflammatory responses (Chinnaiyan, A. M., et al., Science 274:990–2 (1996); Marsters, S. A., et al., Curr Biol 6:1669–76 (1996); Kitson, J., et al., Nature 384:372–5 (1996); Bodmer, J. L., et al., Immunity 6:79–88 (1997); Screaton, G. R., et al., Proc. Natl Acad Sci USA 94:4615–9 (1997); Wallach, D., et al., Annu Rev Immunol 17:331–67 (1999)). TRAF2 is an adapter protein that lies in the TNFα pathway (Rothe, M., et al., Science 269:1424–7 (1995)), while MyD88 functions in the IL-1 and Toll pathways (Medzhitov, R., et al., Mol Cell 2:253–8 (1998)). IKK-i/ε, is an IKK-related kinase that is induced by LPS and is thought to play a role in PMA and TCR-mediated activation of NF-KB (Shimada, T., et al., Int Immunol 11:1357–62 (1999); Peters, R. T., et al., Mol Cell 5:513–22 (2000)).

Nine specific clones encoded the small GTPase rhoB. Like other members of the rho family, rhoB has been known to activate NF-KB when overexpressed (Perona, R., et al., Genes Dev 11:463–75 (1997)) but it is unknown in which pathway it functions. Two clones represented the MARCKS protein, a protein kinase C substrate that interacts with actin and calmodulin and is required for normal brain development (Stumpo, D. J., et al., Proc Natl Acad Sci USA 92:944–8 (1995)). One clone corresponded to Snk, a serum inducible kinase in the polo family (Simmons, D. L., et al., Mol Cell Biol 12:4164–9 (1992)). Neither MARCKS nor Snk have been previously linked to NfKB.

IKK-i/ε was purified from pool 178, the only pool that was inhibited by TBK1 K38A. IKK-i/ε and TBK1 are IKK-related kinases that are most homologous to each other. Both of these kinases activate NF-KB in a kinase-dependent manner, and both interact with the TANK adapter molecule (Pomerantz, J. L. & D. Baltimore, *Embo J* 18:6694–704 (1999); Nomura, F., et al., *Genes Cells* 5:191–202 (2000)). Although the inhibition of IKKi/ε by TBK1 K38A suggested that IKKi/ε might function upstream of TBK1, we found that IKKi/ε K38A can inhibit TBK1 activity as well (data not shown).

Four nonspecific clones were also purified, and found to encode the phosphatase PPX (Hu, M. C., et al., *J Biol Chem* 273:33561–5 (1998)), a fragment (residues 1043–1475) of the nucleoporin NUP153 (McMorrow, I., et al., *Biochim Biophys Acta* 1:219–23 (1994)), the KIAA0122 gene product, which contains two RNP motifs and is likely an RNA-binding protein (Inoue, A., et al., *Nucleic Acids Res* 24:2990–7 (1996)), and C/EBPdelta, a CCAAT-box binding transcription factor (Cao, Z., et al., *Genes Dev* 5:1538–52 (1991)). The precise mechanisms by which these proteins increase luciferase activity in the screen has not been determined.

Thus, provided herein is a useful method for identifying lead targets and/or therapeutics.

TABLE 1

Isolates and representative pool characteristics.

| cDNA | No. isolates | Type | Pathway | Rep. Pool | Igκ$_2$ | MUT | IKKβ K44A | TBK1 K38A | Isolated clone |
|---|---|---|---|---|---|---|---|---|---|
| TRAIL | 1 | ligand | TRAIL | 224 | 3.1 | 0.6 | 1.1 | 3.0 | 19.0 |
| TNFR1 | 2 | recep- | TNFα | 473 | 87.1 | 1.8 | 0.7 | 67.7 | 108.0 |
| TRAM | 4 | tor | Apo3L | 110 | 74.5 | 1.0 | 0.8 | 75.4 | 109.0 |
| P | 2 | recep- | TNFα | 24 | 25.2 | 2.9 | 2.0 | 25.4 | 46.8 |
| TRAF2 | 1 | tor | IL- | 72 | 30.2 | 3.8 | 3.6 | 19.7 | 999.0 |
| MyD88 | 1 | adapter | 1/Toll | 178 | 7.6 | 1.3 | 0.9 | 1.4 | 53.5 |
| IKK-i/ε | 9 | adapter kinas | PMA/T CR | 501 | 3.2 | 0.8 | 0.3 | 2.7 | 20.3 |
| rhoB | 1 | small | | 270 | 6.3 | 1.1 | 1.2 | 5.2 | 24.0 |
| Snk MARC KS | 2 | GTPase kinase kinase substrate | | 525 | 40.9 | 4.4 | 2.9 | 47.0 | 69.0 |

What is claimed is:

1. A method for screening for an agent which modulates transcription factor activity, comprising:
(i) providing a cell comprising a transcription factor of interest and a vector comprising a binding site for said transcription factor of interest operatively linked to a reporter gene;
(ii) introducing a plurality of candidate agents comprising a pool of expression vectors, each comprising transcriptional and translational regulatory nucleic acid operably linked to nucleic acid encoding a polypeptide; and
(iii) determining the activity of said transcription factor by measuring the expression of said reporter gene, wherein a change in activity between the presence and absence of said candidate agents indicates the presence of an agent which modulates transcription factor activity.

2. The method of claim 1, wherein said pool is a cDNA expression library.

3. The method of claim 1, further comprising introducing into said cell a control plasmid comprising a constitutively expressed gene to monitor transfection efficiency.

4. The method of claim 1, wherein said reporter gene is a luciferase gene.

5. The method of claim 1, wherein said reporter gene encodes a fluorescent protein.

6. The method of claim 1, wherein said activity is inhibited.

7. The method of claim 1, wherein said activity is stimulated.

8. The method of claim 1, wherein said cell is a mammalian cell.

9. The method of claim 1, wherein said vector is a mammalian expression vector.

10. The method of claim 1 wherein after a change in activity is determined, said method further comprises the additional steps of dividing said plurality of candidate agents into subsets each containing an individual candidate agent, and introducing said individual candidate agent into an other cell, wherein said other cell comprises a transcription factor of interest and a vector comprising a binding site for a transcription factor of interest operatively linked to a reporter gene, and determining the activity of said transcription factor, wherein a change in activity between the presence and absence of said candidate agent indicates a candidate agent which modulates transcription factor activity.

11. The method of claim 1 wherein after a change in activity is determined, said method further comprises the additional steps of subdividing said plurality of candidate agents into subsets and screening said subsets of candidate agents by individually introducing one of said subsets of candidate agents into an other cell, wherein said other cell comprises a transcription factor of interest and a vector comprising a binding site for a transcription factor of interest operatively linked to a reporter gene, and determining the activity of said transcription factor, wherein a change in activity between the presence and absence of said subset of candidate agents indicates the presence of a candidate agent or candidate agents which modulate transcription factor activity.

12. The method of claim 11, wherein the steps of subdividing said plurality of candidate agents into subsets and screening said subsets is repeated until an individual candidate agent which modulates transcription factor activity is identified.

* * * * *